United States Patent [19]

Lustig et al.

[11] 4,400,160
[45] Aug. 23, 1983

[54] ATRAUMATIC ENDODONTIC RECONSTRUCTION SYSTEM AND PROCESS

[75] Inventors: Leopold P. Lustig, 304 Greenwood St., Newton Centre, Mass. 02159; Alfred H. Rosen, Palm Beach, Fla.

[73] Assignee: Leopold Paul Lustig, Newton Ctr., Mass.

[21] Appl. No.: 318,935

[22] Filed: Nov. 6, 1981

[51] Int. Cl.³ .............................................. A61C 5/02
[52] U.S. Cl. ................................... 433/224; 433/136
[58] Field of Search ........................ 433/81, 224, 136

[56] References Cited

U.S. PATENT DOCUMENTS 3,704,520 12/1972 Weissman .......................... 433/224
4,021,921 5/1977 Detaille ................................ 433/81

Primary Examiner—Robert Peshock
Attorney, Agent, or Firm—Alfred H. Rosen

[57] ABSTRACT

The invention achieves its purposes with a grommet thimble incorporating a bore sleeve which may be fitted with retainer means for a sanitary dam. When this thimble is fitted into the specially-prepared entrance portion of a root canal, the retainer means extends from the tooth for holding a dam of rubber or the like without injury to surrounding gingiva during placement of a clamp for the rubber dam. The root canal can be prepared with the sleeve and dam in place, the sleeve and dam serving to facilitate the establishment and maintenance of a sterile field of operation without creation of unnecessary lacerations on the surrounding gingiva. After completion of the desired preparation procedure, or of partial completion, a temporary plug can be removably fitted into the sleeve protection of the work done or in process. For completion of a restoration several options are available. The retainer means can be left in place and used to anchor a core with or without a post. Alternatively a post can be fastened (e.g. screwed) into the sleeve, with or without keeping the retainer means.

15 Claims, 16 Drawing Figures

ATRAUMATIC ENDODONTIC RECONSTRUCTION SYSTEM AND PROCESS

BACKGROUND OF THE INVENTION

In the setting of endodontic posts in root canals for support of reconstructions it is important to provide a sanitary environment for the preparation of root canals and following procedures, and equally important to prevent cracking or splitting of the root. This invention relates to a new endodontic reconstruction system which is both therapeutic and protective and atraumatic in use.

Recent years have seen an emphatic surge of using root canal therapy as a means of retaining teeth which otherwise would have to be extracted. Problems of how best to strengthen the endodontically treated tooth to make it a viable component of the mouth are the factors limiting the use of root canal therapy. It is recognized to be a sound, preventive measure to reinforce endodontically treated teeth; and reinforcement is considered mandatory if these teeth are to be crowned or serve as abutments. Preventing fracture is less expensive than replacing a fractured tooth. A pulpless tooth becomes brittle, and use of threaded dowels often fractures the root. A precision fitting dowel has a tendency to exert lateral forces when it is cemented. These problems among others are described in the current literature, of which the following articles are representative:

1. "An endodontic-prosthodontic approach to internal tooth reinforcement"—Sapone and Lorencki—The Journal of Prosthetic Dentistry Vol. 45, No. 2, Feb. 1981, pages 164–174;
2. "In vitro analysis of self-shearing retentive pins'-'—Collard, Caputo, Standlee, and Duncanson—The Journal of Prosthetic Dentistry Vol. 45, No. 2, Feb. 1981, pages 156–159.

From the standpoint of endodontic practice care must be exercised during mechanical instrumentation if showers of bacteria are not to be forced through the apical foramen. The root canal surface must be thoroughly sterilized and filled if toxic effect upon the periapical tissue is to be prevented. It is recognized that if the root canal surface is rendered sterile and the canal is well-filled, repair of destroyed periapical bone will take place, and the pulpless tooth need not be looked upon as a hazard to health. In order to maintain a sterile operating technique, the rubber dam is used. It is said to be the only sure safeguard against bacterial contamination from saliva. The currently-known practice for using rubber dams is to isolate the entire tooth containing the root canal to be treated, with attendant injury to surrounding gingiva during placement of a clamp for the rubber dam.

GENERAL DESCRIPTION OF THE INVENTION

The present invention provides solutions to both problems—that of preventing fracture or splitting of roots containing the canal to be treated, and that of isolating that root canal from infection—with a new endodontic reconstruction system which is both therapeutic and atraumatic in use. In general the invention provides a grommet thimble which in use is fitted into the hole of larger bore than the root canal which is opened in the entrance portion of the canal. The root canal is prepared through the grommet thimble for receiving a reconstruction post. A sanitary dam is fitted to the outer periphery of the grommet thimble, so as to isolate the root canal alone, without the need to isolate the entire tooth or to involve the surrounding gingiva in the clamping procedure. After the canal has been prepared, a reconstruction post is fitted through the same or another grommet thimble, which then functions to reinforce the tooth structure against fracture or cracking. During preparation of the canal, and before fitting a reconstruction to the tooth, a temporary plug can be removably fitted into the grommet thimble for protection of the work done or in process, and to maintain asepsis of the canal.

The invention is further illustrated through a description of presently-preferred embodiments which follows.

DETAILED DESCRIPTION OF THE DRAWINGS

Figure 1:
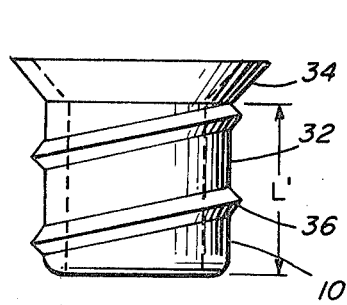
FIG. 1 shows a grommet thimble according to the invention.
Figure 2:
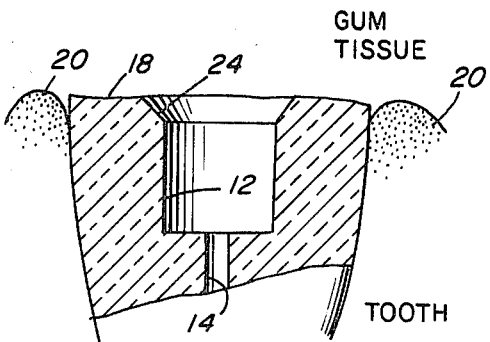
FIG. 2 shows a root canal in a tooth prepared to receive a grommet thimble in its entrance portion.
Figure 3:
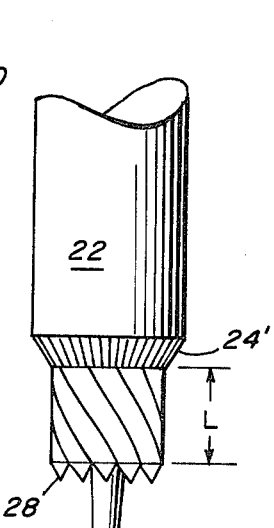
FIG. 3 shows a tool useful to prepare the entrance portion of a root canal as is shown in FIG. 2.

The grommet thimble 10 which is shown in FIG. 1 is intended to be fitted into the entrance portion 12 of (e.g.) the root canal 14 which is shown in FIG. 2. The tooth 16 has been smoothed off at the surface 18 essentially flush with the level of the surrounding gum tissue 20. The entrance portion 12 is bored out to a diameter wider than the root canal 14, using a special tool 22 such as is illustrated in FIG. 3. With this tool a bevel 24 is formed at the outer margin of the entrance portion 12, using the bevel-grinder 24'. The main body 26' of the tool grinds the entrance portion 12 to the desired diameter. The bottom teeth 28' grind a shelf 28 at the bottom of the entrance portion. A smooth centering guide 30 of the tool fits in the canal 14 and centers the tool for preparing the wide opening in the entrance portion 12.

The grommet thimble 10 is a sleeve which lines the entrance bore 12. It is fitted with a flared band 34 at its outer end, for engaging the bevel 24 when the sleeve is fully seated in the entrance portion 12. The outer side surface 32 of the sleeve may be fitted with self-tapping threads 36, so that the grommet thimble may be screwed into the entrance portion 12 of the root canal.

Figure 4:
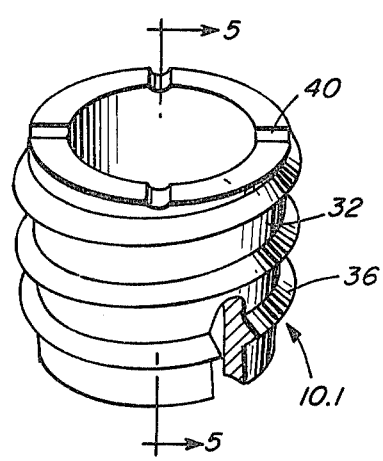
FIG. 4 shows another grommet thimble.
Figure 5:
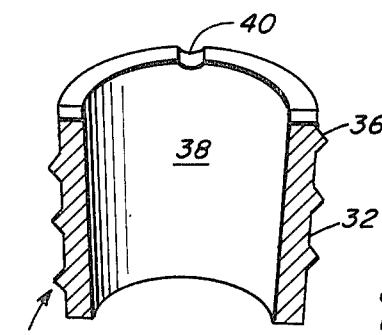
FIG. 5 is an axial section through FIG. 4.

FIGS. 4 and 5 show a grommet thimble 10.1 which is similar to the thimble 10 of FIG. 1 but lacks the flared band 34. The inner surface 38 is shown smooth but as will be seen in FIGS. 11 and 12 the inner surface can be threaded, if desired. Slots 40 at the outer edge are provided to engage a screwdriver; similar screw-driver engagement means may be provided in FIG. 1.

Figure 6:
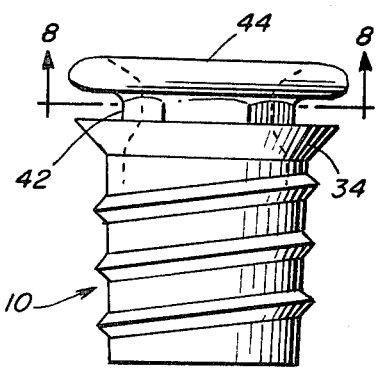
FIG. 6 shows a grommet thimble fitted with retaining means for a sanitary dam.
Figure 8:
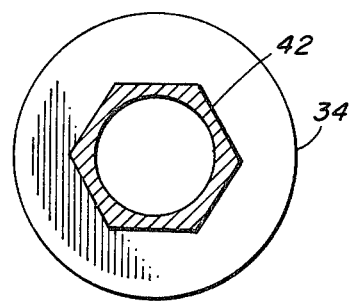
FIG. 8 is a transverse section taken on line 8—8 of FIG. 6.
Figure 9A:
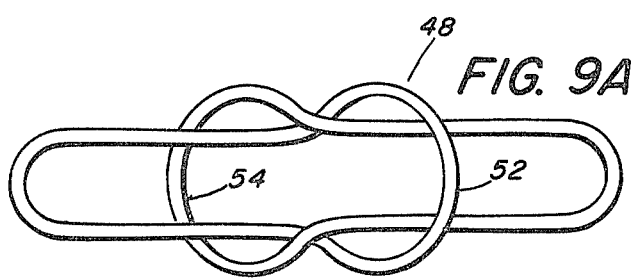
FIG. 9A shows another sanitary dam clamp.

FIG. 6 shows the grommet thimble 10 fitted at its outer periphery with a collar 42 and an outwardly flared ring 44 under which a sanitary dam (shown in FIG. 10) can be retained at the entrance to the root canal 14. The collar has for example a hexagonal outer periphery, shown in FIG. 8, for cooperating with a clamp 46 shown in FIG. 9. FIG. 9A shows another form of clamp 48 made of two U-shaped wire components 52, 54 cooperating in the manner of a square knot, which is adjustable to form a loop around the collar 42.

Figure 7:
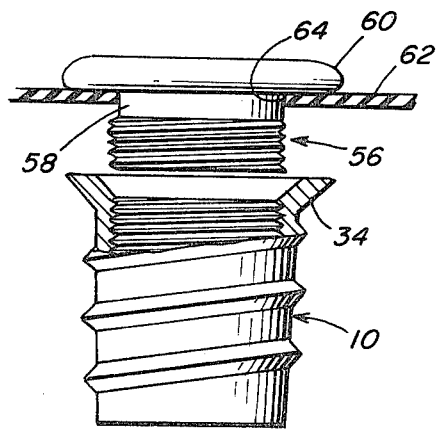
FIG. 7 shows another grommet thimble fitted with removable retaining means for a sanitary dam.

As is shown in FIG. 7, the grommet thimble 10 can be internally threaded at its outer end, and a dam retainer 56 can be removably fitted to it. This retainer has a round collar 58 which can be threaded into the thimble-sleeve, and flared ring 60. A sanitary (e.g. rubber) dam 62 has a small perforation 64 through which the collar 58 is fitted and then screwed into the grommet thimble 10, retaining the dam between the flared end 34 and the flared ring 60.

Figure 9:
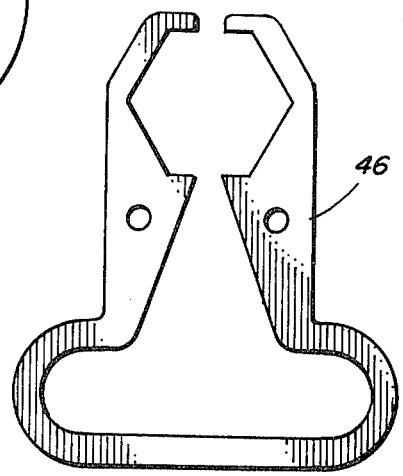
FIG. 9 is a sanitary dam clamp useable to place a dam on the grommet thimble according to FIG. 6.
Figure 10:
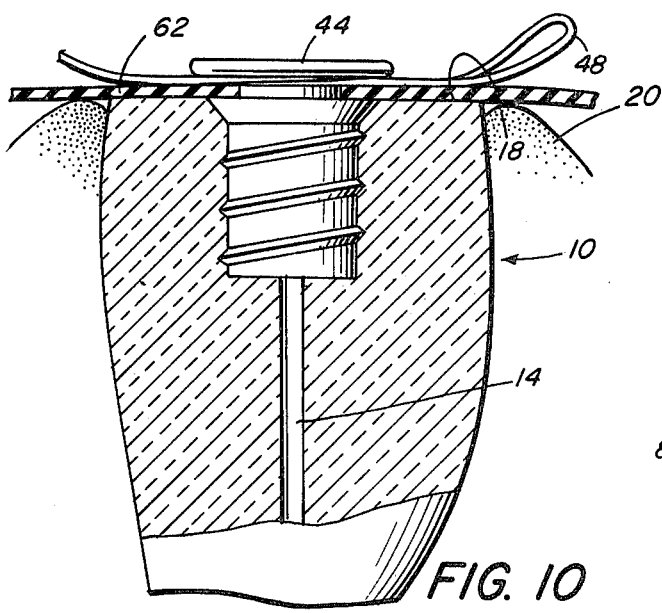
FIG. 10 shows a grommet thimble according to FIG. 6 installed in a root canal retaining a sanitary dam at the entrance to the root canal.
Figure 12:
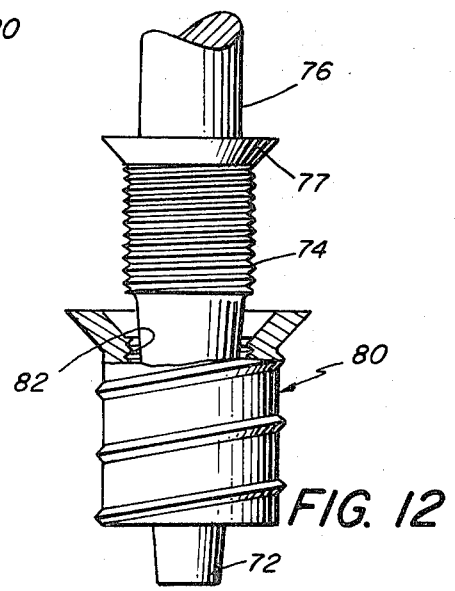
FIG. 12 shows a reconstruction pin threadedly engageable in a grommet thimble.
Figure 11:
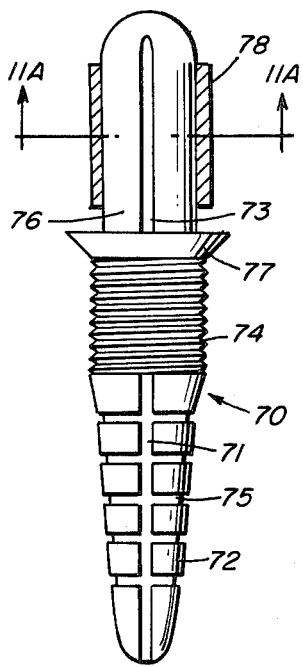
FIG. 11 shows a reconstruction pin according to the invention, with a transfer sleeve.
Figure 11A:
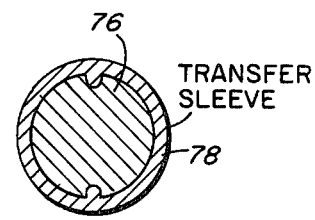

As is shown in FIG. 10, when a grommet thimble 10 with fixed retainer means 42,44 according to FIG. 6 is used, the dam 62 is slipped over the flared ring 44 and is held down on the tooth with a clamp such as the clamp 46 shown in FIG. 9. In either case, FIG. 10 or FIG. 7, the dam 62 is held in place by retainer means fitted to the grommet thimble 10, and it isolates the root canal from the outer surface 18 of the tooth and from the surrounding tissue 20, without the need to isolate the entire tooth or to involve the surrounding gingiva in the clamping procedure. Once in place, the grommet thimble 10 (or 10.1 or other) protects the surrounding dentin mechanically. The root canal 14 can be prepared through it, and it can accommodate a removable seal or a cap (not shown) to function as a temporary plug for protecting the root canal from infection and maintaining asepsis of the canal during interruption of the reconstruction procedure. After the root canal has been prepared, the grommet thimble, or a substitute, can be used to retain or support a reconstruction post, or the like in place in the root canal. FIGS. 11 and 11A show a reconstruction post 70 which can be used in practising the invention. This post has an intra-coronal pin 72 for fitting inside the canal 12, an externally threaded support body 74 intended to be threaded into an internally-threaded grommet thimble 80 (as is shown in FIG. 12 and described following), and an extra-coronal part 76 which is shown fitted with an optional transfer sleeve 78. Vent-grooves 71,73 are fitted to the pin 70, as well as depth-gauge grooves 75. The support body 74 has a flared top seal 77, for seating on the flared band 84 of the grommet thimble 80 when the support body is fully threaded into the grommet thimble, and thereby sealing the opening to the root canal. The grommet thimble 80 has external self-tapping threads 86 for engaging in the tooth dentin, like the grommet thimble 10 as shown in FIG. 10. The internal threads 82 engage the threads of the support body 74 of the pin 70, and in this manner the pin 70 is fastened into a root canal such as the canal 14 shown in FIG. 10, and the opening into the canal is sealed with the top seal 77. The finished installation will be similar to that shown in FIG. 14. A reconstruction can be built on the extra-coronal portion 76 in any desired fashion; the invention facilitates use of a transfer sleeve 78, if desired.

Figure 13:
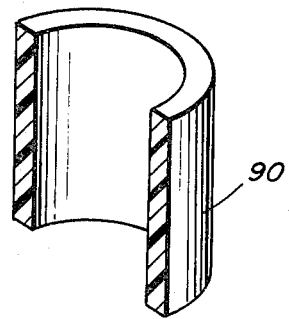
FIG. 13 shows another embodiment of a grommet thimble.

Grommet thimbles useful to support a reconstruction pin according to the invention can be made of any desired material. FIG. 13 shows a grommet thimble 90 which is made of a simple sleeve of a ceramic or like material, roughened but not threaded on its inner or outer surface. This sleeve can be cemented into the entrance portions 12 of a root canal 14, and a recontruction pin can be cemented into it. Such a sleeve can facilitate the use of core-paste reconstructions, and can give added strength to a crown or jacket which is supported on a core-paste reconstruction.

Figure 14:
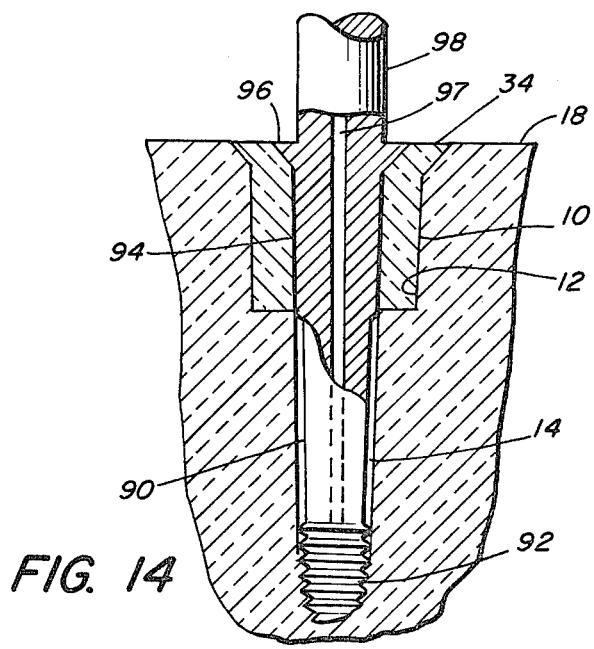
FIG. 14 shows an assembly of a pin and a grommet thimble in a root canal, wherein certain additional capabilities of the invention are illustrated.

FIG. 14 shows a grommet thimble 10 which is smooth internally cooperating to support, but not to retain in place, a reconstruction pin 90 in the root canal 14. External threads are not shown on the grommet thimble 10, but it will be understood that such threads may be present if desired. The pin 90 has an intra-coronal part 91 which has threads 92 at its lower extremity, by which the pin is engaged into the dentin. The support body 94 is without threads on its outer surface, and fits slidingly within the grommet thimble 10, where it can be cemented in place if desired. A top seal 96 engages the flared band 34 when the pin is seated by the threads 92. The extra-coronal part 98 is available to suport a dental reconstruction.

The pin 90 has an axial bore 97 running from the extra-coronal part 98 through the support body 94 and the intra-coronal part 91 to the bottom of the root canal 14 when the pin is in place in the root canal. This bore can be used for augmentation of retention, as well as for venting, or for treatment purposes. If the intra coronal part 91 is made of a light-transmissive material, or if light is passed through the bore 97, dental materials which can be light-activated (e.g. by U.V. light) can be used to form solid seals at the bottom of the root canal, and to retain a reconstruction pin in the rootcanal. The threads 92 can be engaged in such a seal, as an alternative to threading them into the dentin.

The invention achieves its pruposes with a grommet thimble incorporating a bore sleeve which may be fitted with retainer means for a sanitary dam. When this thimble is fitted into the specially-prepared entrance portion of a root canal, the retainer means extends from the tooth for holding a dam of rubber or the like without injury to surrounding gingiva during placement of a clamp for the rubber dam. The root canal can be prepared with the sleeve and dam in place, the sleeve and dam serving to facilitate the establishment and maintenance of a sterile field of operation without creation of unnecessary lacerations on the surrounding gingiva. After completion of the desired preparation procedure, or of partial completion, a temporary plug can be removably fitted into the sleeve protection of the work done or in process. For completion of a restoration several options are available. The retainer means can be left in place and used to anchor a core with or without a post. Alternatively a post can be fastened (e.g. screwed) into the sleeve, with or without keeping the retainer means. The latter procedure has been illustrated, but it will be understood that the former procedure is also possible, in which case paste-like materials which are self-hardening (e.g. corepaste) can be used.

We claim:

1. A grommet thimble for use in preparing a root canal of a tooth for endodontic reconstruction of said tooth comprising a tubular body of solid material having an outer diameter greater than the diameter of said root canal and an axial length which is a small fraction of the depth of said root canal for fitting into and lining an entrance hole of larger bore than the root canal in the entrance portion of the canal, said tubular body having an inner bore the diameter of which is substantially the same as the inner diameter of said canal giving access to said canal for purposes including preparation and reconstruction, including flanged-collar means at the periphery of the end which remains outside said entrance hole when said thimble is installed therein, said flanged collar means overlying an annular recess which is open for receiving and for retaining in said recess a sanitary dam having a perforation in register with said inner bore, so as to cover said tooth and the surrounding gingiva with said dam while giving access to said root canal through said perforation and said bore, and, clamp means engageable under said collar for holding said sanitary dam in a desired location.

2. A grommet thimble according to claim 1 having screw-threads on its outer tubular surface, for threadedly fixing said thimble in said entrance hole.

3. A grommet thimble according to claim 2 having a substantially smooth inner bore.

4. A grommet thimble according to claim 2 having a screw-threaded inner bore.

5. A grommet thimble according to claim 2 having a roughened surface on its inner bore.

6. A grommet thimble according to claim 1 including a separable collar threadedly engageable inside said inner bore at said end, for fitting through said perforation of said dam and, when threaded into said bore, retaining said dam with said perforation in register with said bore.

7. For use in the combination according to claims 1 a clamp in the form of a wire loop, and means to alter the size of said loop from a size capable of fitting over said collar to a fixable size tightly embracing said retaining means under said collar.

8. In combination, a grommet thimble for use in preparing a root canal of a tooth for endodontic reconstruction of said tooth, and a reconstruction pin adapted to be installed in said root canal, said grommet thimble comprising a tubular body of solid material having an outer diameter greater than the diameter of said root canal and an axial length which is a minor fraction of the depth of said root canal for fitting into and lining an entrance hole of larger bore than the root canal in the entrance portion of the canal and giving support to the dentinal material surrounding said entrance hole, said tubular body having an inner bore the diameter of which is substantially the same as the inner diameter of said canal giving access to said canal through said inner bore, said reconstruction pin having a support portion adapted to fit mating-wise into said inner bore for supporting said reconstruction pin in said grommet thimble, means to support an extra-coronal reconstruction, and a canal portion extending from said support portion for penetrating a prepared root canal to a prescribed depth measured from said grommet thimble.

9. A combination according to claim 8 in which said grommet thimble has a screw-threaded inner bore, and said reconstruction pin has corresponding screw threads on the outer periphery of its support portion, for engaging said reconstruction pin in said grommet thimble with capability to adjust the penetration into said canal of said canal portion of said reconstruction pin.

10. A combination according to claim 8 in which said canal portion of said reconstruction pin has means at its apical end for engaging in the bottom of said prepared root canal.

11. A combination according to claim 10 in which said apical end is threaded.

12. A combination according to claim 11 in which said support portion is free of engagement means and fits slidingly within said inner bore of said tubular body.

13. A combination according to claim 8 in which at least said canal portions of said reconstruction pin is axially hollow.

14. A combination according to claim 8 in which said pin is adapted to conduct light in the range including at least the visible and ultra-violet frequency bands.

15. Method of preparing a root canal of a tooth for endodontic reconstruction of said tooth comprising the steps of opening a hole of larger bore than the root canal in an entrance portion of the canal, lining said hole with a grommet thimble, fitting said grommet thimble with a sanitary dam covering said tooth and the surrounding gingiva, providing an opening into said grommet thimble through said flexible dam, and preparing said canal through said opening and said grommet thimble.

* * * * *